(12) United States Patent
Harjunmaa et al.

(10) Patent No.: US 10,234,386 B2
(45) Date of Patent: Mar. 19, 2019

(54) NEPHELOMETER

(71) Applicants: Hannu Harjunmaa, Holden, MA (US);
Enni Harjunmaa, Holzgerlingen (DE)

(72) Inventors: Hannu Harjunmaa, Holden, MA (US);
Enni Harjunmaa, Holzgerlingen (DE)

(*) Notice: Subject to any disclaimer, the term of this patent is extended or adjusted under 35 U.S.C. 154(b) by 0 days.

(21) Appl. No.: 15/674,308

(22) Filed: Aug. 10, 2017

(65) Prior Publication Data

US 2018/0045643 A1 Feb. 15, 2018

Related U.S. Application Data

(60) Provisional application No. 62/373,280, filed on Aug. 10, 2016.

(51) Int. Cl.
*G01N 21/51* (2006.01)
*G01N 21/49* (2006.01)
*G01N 21/59* (2006.01)

(52) U.S. Cl.
CPC .......... *G01N 21/51* (2013.01); *G01N 21/49* (2013.01); *G01N 21/59* (2013.01); *G01N 2201/0221* (2013.01); *G01N 2201/0662* (2013.01)

(58) Field of Classification Search
CPC .. G01N 21/51; G01N 21/532; G01N 15/1459; G01N 2015/008; G01N 15/0205; G01N 15/147; G01N 2015/0073; G01N 2015/0076; G01N 2021/0346; G01N 21/53; G01N 2015/0084; G01N 2021/4735; G01N 21/03
See application file for complete search history.

(56) References Cited

U.S. PATENT DOCUMENTS

| | | | | |
|---|---|---|---|---|
| 4,541,719 A * | 9/1985 | Wyatt | ............... | G01N 21/47 356/343 |
| 5,350,922 A * | 9/1994 | Bartz | ............... | G01N 21/49 250/338.5 |
| 5,828,458 A * | 10/1998 | Taylor | ............... | G01N 21/532 356/440 |
| 7,551,277 B2* | 6/2009 | Cole | ............... | G01F 1/6842 356/335 |
| 2010/0225920 A1* | 9/2010 | Xia | ............... | B01L 9/06 356/442 |
| 2012/0194800 A1* | 8/2012 | Debreczeny | ............... | G01N 15/06 356/51 |

* cited by examiner

*Primary Examiner* — Michael P Stafira
(74) *Attorney, Agent, or Firm* — Gerry A. Blodgett; David J. Blodgett; Blodgett & Blodgett, P.C.

(57) ABSTRACT

A nephelometer for determining the turbidity of a body of fluid in which a light beam is directed as an angled beam through the body and two light detectors measure the intensity of light scatter at two points in the beam. The two measurements are divided and scaled, and then the result is logarithmically amplified and displayed as the turbidity.

30 Claims, 3 Drawing Sheets

NEPHELOMETER

CROSS-REFERENCE TO RELATED APPLICATIONS

This application claims the benefit under 35 U.S.C. § 119(e) and § 120 of U.S. Provisional Application No. 62/373,280 filed Aug. 8, 2016, the entire contents of which is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

This invention is a nephelometer.

BACKGROUND OF THE INVENTION

There are many situations in which it is necessary to monitor the turbidity of a body of fluid. Turbidity is the cloudiness or haziness of a fluid caused by large numbers of individual particles. This invention relates to the measurement of turbidity, or cloudiness, in liquids held in a receptacle, such as a bottle. One common use of a measurement of turbidity is in monitoring cell cultures in microbiology laboratories. The higher the turbidity, the higher the cell number density in the cell culture. The description of the invention will be in the context of cell culture; however, this patent application is intended to cover many other uses where turbidity needs to be measured, in laboratory and field work, in medicine, in various industries such as pharmaceutical, food, beverage etc., as well as hydrology, in general, and drinking water quality control in particular.

The prevalent method of monitoring a cell culture, for instance, of *Escherichia Coli* bacteria, in order to detect the right time for an intervention, is to take out a sample using a pipette, and to insert the sample in a cuvette that is then inserted in a spectrophotometer for turbidity measurement. There are drawbacks to this method. First of all, it exposes the cell culture to the risk of contamination. Secondly, it takes time. Minor nuisances of the conventional method include the partial loss of culture due to sampling, the expense of a pipette tip, and the need to wash the cuvette.

BRIEF SUMMARY OF THE INVENTION

This invention is a nephelometer and method of using it for quantifying the turbidity in a body of fluid. The nephelometer has light source, with a beam of light from the light source and extending a distance through a body of fluid. The beam has a first point along the distance and a second point along the distance, separated from the first point. A first scattered light detector detects the amount of light scattered at the first point, and produces a first signal representing the amount of light received by the first scattered light detector. A second scattered light detector that detects the amount of light scattered at the second point, and produces a second signal representing the amount of light received by the second scattered light detector. A division device produces a third signal equal to the ratio between the first signal and the second signal. A logarithmic amplifier device that produces a fourth signal from the third signal and representing the concentration of the turbidity of the body of fluid. A display that presents the turbidity in a body of fluid.

BRIEF DESCRIPTION OF THE DRAWINGS

The character of the invention, however, may best be understood by reference to one of its structural forms, as illustrated by the accompanying drawings, in which.

DETAILED DESCRIPTION OF THE INVENTION

Figure 1:
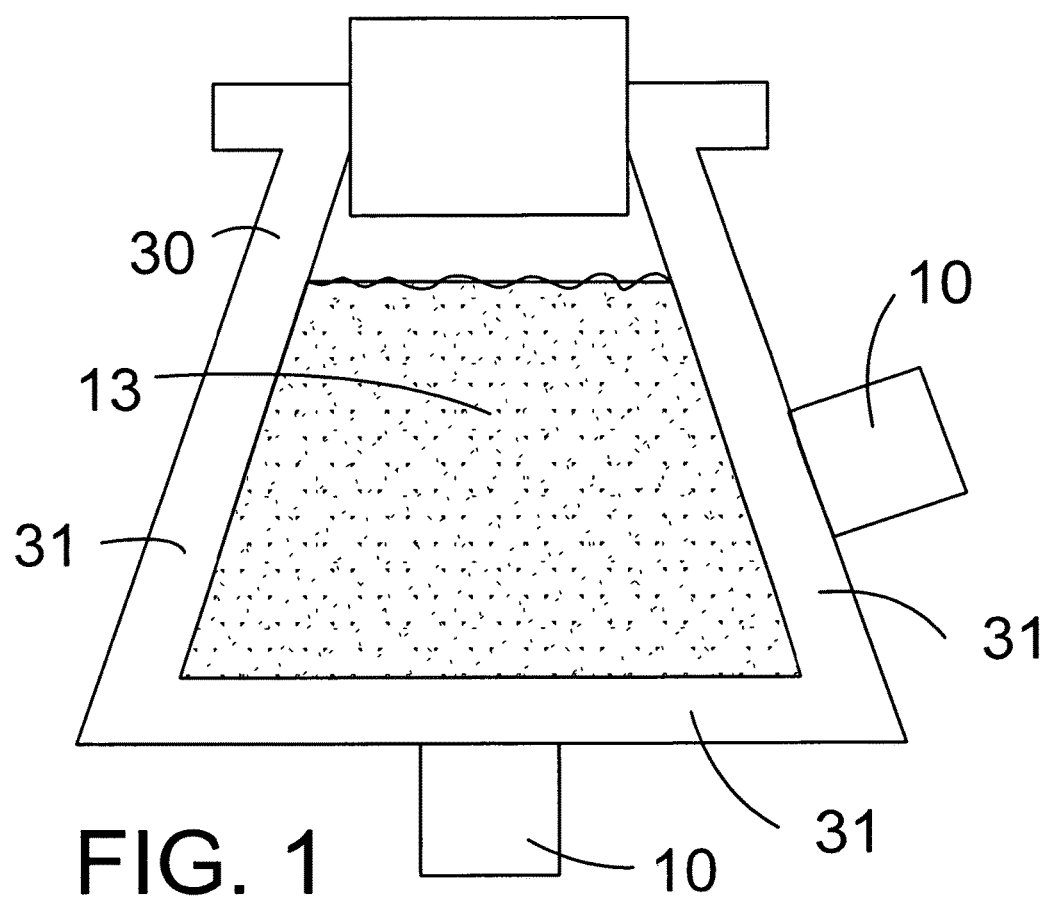
FIG. 1 is a perspective view of a nephelometer embodying the principles of the present invention, attached to the side or the bottom of a container containing the body of fluid to be measured.

Referring first to FIG. 1 in which the general principles of the present invention are shown, FIG. 1 shows the manner in which the user uses the present invention 10 to replace the turbidometric measurement in a spectrophotometer with a nephelometric measurement using a hand-held device 10 that performs a nephelometric measurement through the wall 31 of the cell culture receptacle 30, often an Erlenmeyer flask, filled with the cell culture 13.

Turbidometry measures the loss of light in a transmitted light beam due to scattering off the cells in the culture. Nephelometry measures the amount of light scattered off the cells. By calibration, the two measurement results can be made equivalent.

Figure 2:
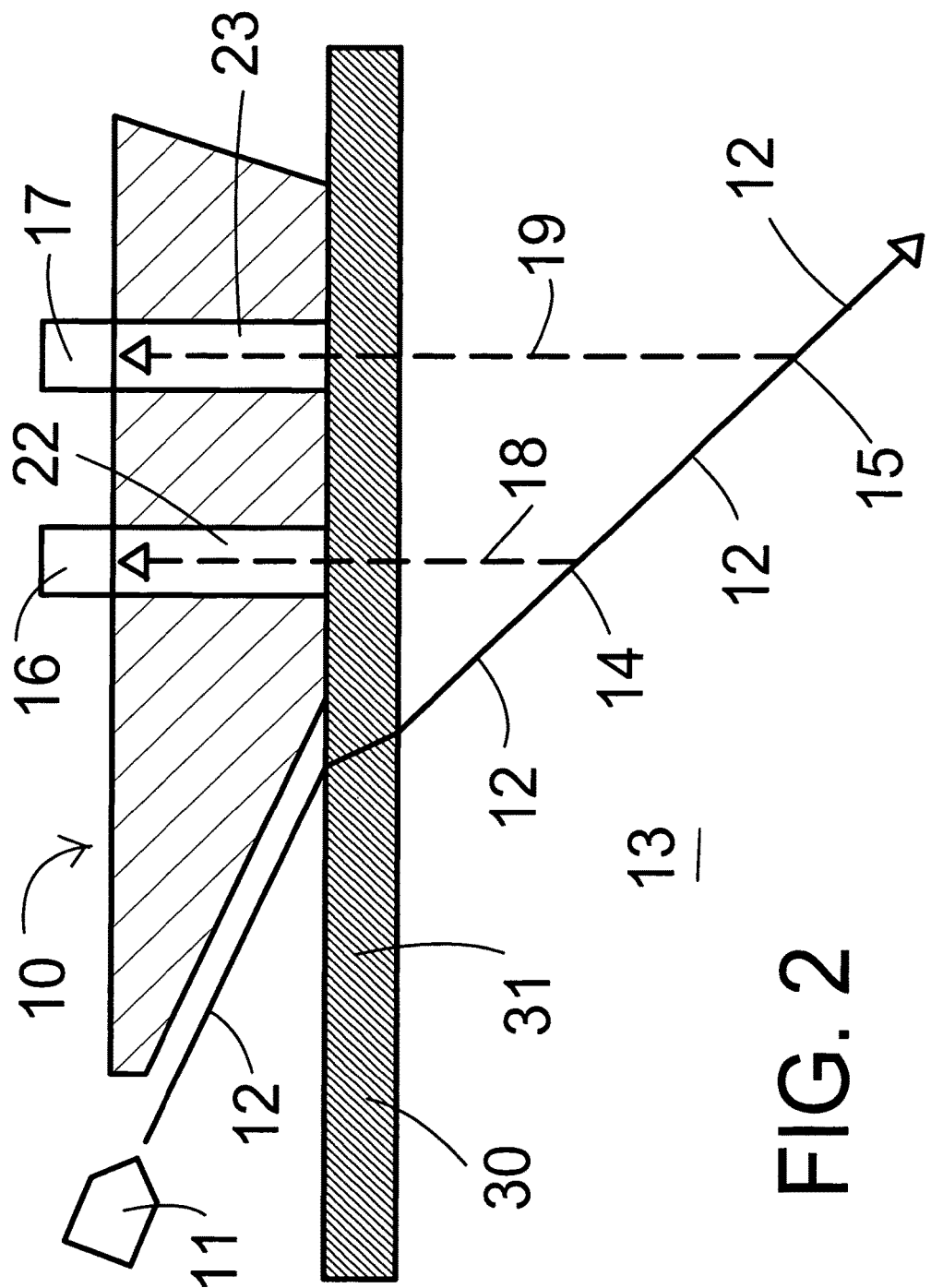
FIG. 2 is a schematic sectional side view of a nephelometer embodying the principles of the present invention.

Referring to FIG. 2, using the light beam 12 of the nephelometer 10 through the wall 31 of the container 30 eliminates the possibility of contamination in the cell culture 13, which is important if the result of the culture is unexpected in one way or another, the researcher faces a great difficulty figuring out what might be the reason for the unexpected result. It may be contamination, or it could be something else. If the possibility of contamination is excluded by never opening the culture flask, the researcher can focus on truly relevant factors behind the unexpected result.

Description of the Preferred Embodiment of the Nephelometer Device

In the preferred embodiment, the light 12 necessary to perform the measurement emanates from a Light-Emitting Diode (LED) or laser source 11. A narrow beam is directed into the bottle or flask 30 containing the culture solution 13 at an angle that is 35 to 55 degrees, preferably 45 degrees from the normal of the inside wall 31 in the solution. That angle in an aqueous solution is achieved by directing the beam at an angle of 60 to 80 degrees and preferable 70° from the normal to the outside wall 31 in air outside of the flask. In this preferred embodiment, the LED light 12 is modulated (chopped) in order to minimize the effect of ambient light.

Figure 3:
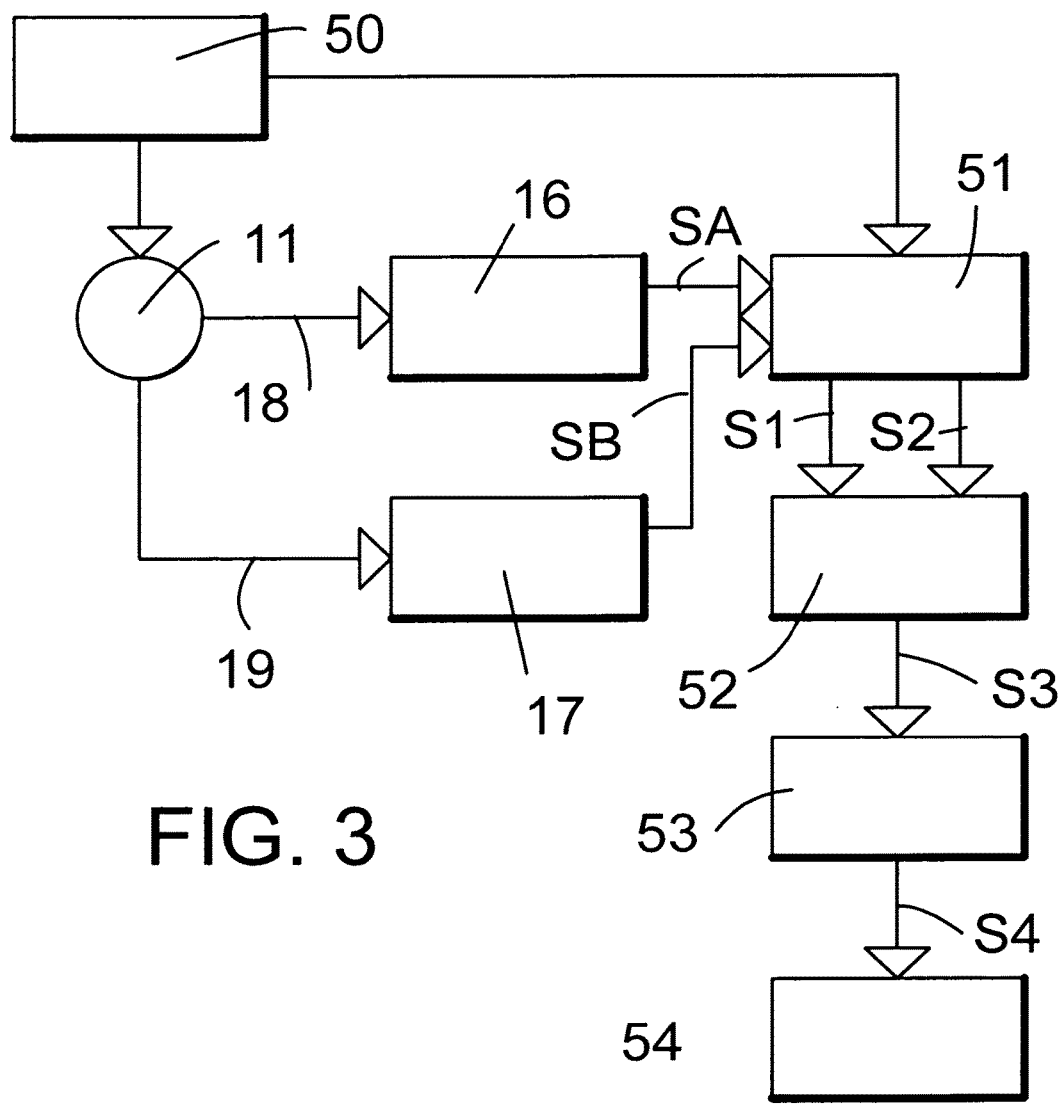
FIG. 3 is a flow chart of the operation a nephelometer embodying the principles of the present invention.

Two photodetectors 16 and 17 detect the scattered light 18 and 19 respectively from the cells in the culture 13. The photodetectors 16 and 17 are arranged to see only a short fraction of the illuminating beam 12 at two different distances 14 and 15 from the light source 11. The two scattered light beams signals 18 and 19 are received by the scattered light detectors 16 and 17 respectively. The intensity of the scattered light actually received by each of the photodetectors is easily derived from the basic equation:

$$I = I_0 \exp(-sx) \quad (1)$$

where
I=detected intensity from the beam 12
$I_0$=initial intensity on a point of the beam 12
s=scattering coefficient
x=distance traveled Referring to FIG. 3, The detectors 16 and 17 convert the received beam intensity of the beams 18 and 19, respectively, into signals SA and SB respectively. After rectification in rectifier 51, the signals SA and SB become S1 and S2, respectively. From the function of the two signals S1 and S2, the ratio of the two received signals as determined by divider 52 and is approximately proportional to the number density N of scatterers in the solution, in the absence of absorption, which is generally the case in cell cultures.

$$N = S1/(S2+C) \quad (2)$$

The value of the constant C is determined by actual measurements of several number density levels.

To obtain the corresponding Optical Density OD, which is a commonly used measure of the growth of the cell culture, the number density N is converted to Optical density OD, by the expression OD=k log(N) using a log amplifier 53 or a processor (k is a calibration constant which, in this analog embodiment, is set with a potentiometer).

It is to be noted that the calculated result is approximately in the form of a ratio, and is therefore robust against changes in the intensity of the light beam, which could result from absorption at the air/glass/culture interfaces, battery discharge etc.

Another notable characteristic of the invention is that all of the signal processing can be done in analog circuits, with no need for a digital processor and therefore, no need for software. This makes it possible to produce a device according to this invention for a very low cost. In high volume production, however, digital circuitry and digital computing devices would be used the make these calculations, instead of analog devices.

Further Description of the Accompanying Figures

FIG. 2 depicts the optical arrangement. Light source 11 generates the light beam 12 that propagates in the culture medium 13 at a 45° angle from the normal of the inside of the wall 31 of the container 30. The narrow fields of view of detectors 16 and 17 are mounted at the outboard ends of narrow channels 22 and 23, respectively, to allow the detectors to see only a narrow angle of the light scattered at two different locations 14 and 15 along the beam 12.

FIG. 3 is a block diagram of the system. System clock 50 generates the square wave that controls the LED or laser light source 11, as well as the synchronous rectification circuit 51. Detectors 16 and 17 detect the scattered light at separate points 14 and 15 on the beam 12 in the culture medium 13, to produce received scattered light intensity signals SA and SB. These intensity signals are rectified by synchronous rectifier 51 into signal S! And S2. A division circuit 52 performs the division of equation 2, to product signal S3, which is proportional to the particle Number Density at points 14 and 15 on the beam 12. A logarithmic amplifier 53 converts the signal S3 to a logarithmic value that corresponds to the Optical Density which is the value obtained with a spectrophotometer of the conventional method. Display unit 54 displays the result in Optical Density units.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desire to secure by Letter Patent is:

1. A nephelometer for quantifying the turbidity in a body of fluid, comprising:
   a. a light source
   b. a beam of light from the light source and extending a distance into the body of fluid,
      i. said beam having a first point along the beam and in the fluid and
      ii. said beam having a second point along the beam and in the fluid, separated from the first point, and located more deeply into the medium than the first point,
   c. a first scattered light detector that detects the amount of light scattered from the beam at the first point, and produces a first signal representing the amount of light received by the first scattered light detector,
   d. a second scattered light detector that detects the amount of light scattered from the beam at the second point, and produces a second signal representing the amount of light received by the second scattered light detector,
   e. a division device that produces a third signal equal to the ratio between the first signal and the second signal,
   f. a logarithmic amplifier device that produces a fourth signal from the third signal and representing the concentration of the turbidity of the body of fluid, and
   g. a display that presents the turbidity in the body of fluid.

2. A nephelometer as recited in claim 1, wherein the logarithmic amplifier device converts the particle number density of the body of fluid to the optical density.

3. A nephelometer as recited in claim 1, wherein the nephelometer is positioned outside of a container holding the body of fluid, and adjacent the outside surface of a wall of the container.

4. A nephelometer as recited in claim 1, wherein the nephelometer is positioned outside of a transparent container holding the body of fluid, and adjacent the outside surface of a wall of the container.

5. A nephelometer as recited in claim 1, wherein the nephelometer is positioned outside of a transparent container holding the body of fluid, and adjacent the outside surface of a bottom wall of the container.

6. A nephelometer as recited in claim 1, wherein the light source produces a chopped beam to minimize the effect of ambient light.

7. A nephelometer as recited in claim 1, wherein the scatter light detectors are designed to measure a small angle of scattered light.

8. A nephelometer as recited in claim 1, wherein the scatter light detectors are designed with a conduit the restricts measurement of scattered light to a small angle.

9. A nephelometer as recited in claim 1, wherein the nephelometer is portable.

10. A nephelometer as recited in claim 1, wherein the nephelometer is handheld.

11. A nephelometer as recited in claim 1, wherein the nephelometer is battery powered.

12. A nephelometer as recited in claim 1, wherein the beam of light extends to the wall of the container at an angle of 60 to 80 degrees from the normal of the outside of the container wall.

13. A nephelometer as recited in claim 1, wherein the beam of light extends to the wall of the container at an angle of 70 degrees from the normal of the outside of the container wall.

14. A nephelometer as recited in claim 1, wherein the beam of light extends through the fluid at an angle of 35 to 55 degrees from the normal of the inside of the container wall.

15. A nephelometer as recited in claim 1, wherein the beam of light extends through the fluid at an angle of 45 degrees from the normal of the inside of the container wall.

16. A method for quantifying the turbidity in a body of fluid using a nephelometer, the method, comprising:
   a. shining a beam of light from a light source, the beam extending a distance into the body of fluid,
      i. said beam having a first point along the beam and in the fluid and
      ii. said beam having a second point along the beam and in the fluid, separated from the first point, and located more deeply into the medium than the first point,
   b. using a first scattered light detector that detects the amount of light scattered from the beam at the first point, and produces a first signal representing the amount of light received by the first scattered detector,
   c. using a second scattered light detector that detects the amount of light scattered from the beam at the second point, and produces a second signal representing the amount of light received by the second scattered detector,
   d. using a division device to produce a third signal equal to the ratio between the first signal and the second signal,
   e. using a logarithmic amplifier device to produce a fourth signal from the third signal and representing the turbidity of the body of fluid, and
   f. using a display that presents the turbidity value.

17. A method as recited in claim 16, wherein the logarithmic amplifier device converts the particle number density of the body of fluid to the optical density.

18. A method recited in claim 16, wherein the nephelometer is positioned outside of a container holding the body of fluid, and adjacent the outside surface of a wall of the container.

19. A method as recited in claim 16, wherein the nephelometer is positioned outside of a transparent container holding the body of fluid, and adjacent the outside surface of a wall of the container.

20. A method as recited in claim 16, wherein the nephelometer is positioned outside of a transparent container holding the body of fluid, and adjacent the outside surface of a bottom wall of the container.

21. A method as recited in claim 16, wherein the light source produces a chopped beam to minimize the effect of ambient light.

22. A method as recited in claim 16, wherein the scatter light detectors are designed to measure a small angle of scattered light.

23. A method as recited in claim 16, wherein the scatter light detectors are designed with a conduit the restricts measurement of scattered light to a small angle.

24. A method as recited in claim 16, wherein the nephelometer is portable.

25. A method as recited in claim 16, wherein the nephelometer is handheld.

26. A method as recited in claim 16, wherein the nephelometer is battery powered.

27. A method as recited in claim 16, wherein the beam of light extends to the wall of the container at an angle of 60 to 80 degrees from the normal of the outside of the container wall.

28. A method as recited in claim 16, wherein the beam of light extends to the wall of the container at an angle of 70 degrees from the normal of the outside of the container wall.

29. A method as recited in claim 16, wherein the beam of light extends through the fluid at an angle of 35 to 55 degrees from the normal of the inside of the container wall.

30. A method as recited in claim 16, wherein the beam of light extends through the fluid at an angle of 45 degrees from the normal of the inside of the container wall.

* * * * *